United States Patent [19]

White et al.

[11] Patent Number: 4,984,941
[45] Date of Patent: Jan. 15, 1991

[54] APPARATUS FOR FORMING A SUTURE CUT-OFF FEATURE IN A SURGICAL NEEDLE POSSESSING A SUTURE-RECEIVING SOCKET

[75] Inventors: Edward C. White, Orange; Douglas T. Blake, Milford; Michael C. Grassel, New Milford, all of Conn.

[73] Assignee: United States Surgical Corporation, Norwalk, Conn.

[21] Appl. No.: 317,949

[22] Filed: Mar. 2, 1989

[51] Int. Cl.⁵ .............................................. B23B 47/28
[52] U.S. Cl. ........................................... 408/104; 163/5
[58] Field of Search ............... 163/1, 5; 408/110, 112, 408/111, 104, 103, 107, 99, 100; 128/339

[56] References Cited

U.S. PATENT DOCUMENTS

| 1,757,129 | 5/1930 | McClure. | |
| 2,620,028 | 12/1952 | Kohut | 163/5 |
| 2,661,662 | 12/1953 | Hall | 408/107 |
| 2,910,983 | 11/1959 | Everett | 128/339 |
| 3,535,957 | 10/1970 | Ferstle | 408/104 |
| 3,799,169 | 3/1974 | Beroff et al. | 163/1 |
| 3,910,282 | 10/1975 | Messer et al. | 128/339 |
| 3,926,194 | 12/1975 | Greenberg et al. | 163/5 |
| 3,943,933 | 3/1976 | Gertzman | 129/339 |
| 3,949,756 | 4/1976 | Ace | 163/1 |
| 4,054,144 | 10/1977 | Hoffman et al. | 163/5 |
| 4,072,041 | 2/1978 | Hoffman et al. | 163/5 |
| 4,114,484 | 9/1978 | Feamster | 408/104 X |
| 4,319,503 | 3/1982 | Saine et al. | 408/104 X |
| 4,501,312 | 2/1985 | Matsutani | 163/5 |
| 4,799,311 | 1/1989 | Matsutani | 163/1 |
| 4,805,292 | 2/1989 | Noguchi | 163/5 |

FOREIGN PATENT DOCUMENTS

| 973795 | 6/1960 | Fed. Rep. of Germany | 408/104 |
| 20487 | 2/1977 | Japan | 408/104 |
| 94231 | 5/1985 | Japan | 163/5 |
| 916121 | 3/1982 | U.S.S.R. | 408/104 |

Primary Examiner—William Briggs
Attorney, Agent, or Firm—Thomas R. Bremer; Peter G. Dilworth; Rocco S. Barrese

[57] ABSTRACT

An apparatus is provided for accurately forming suture cut-off feature in a surgical needle of the socketed type.

11 Claims, 3 Drawing Sheets

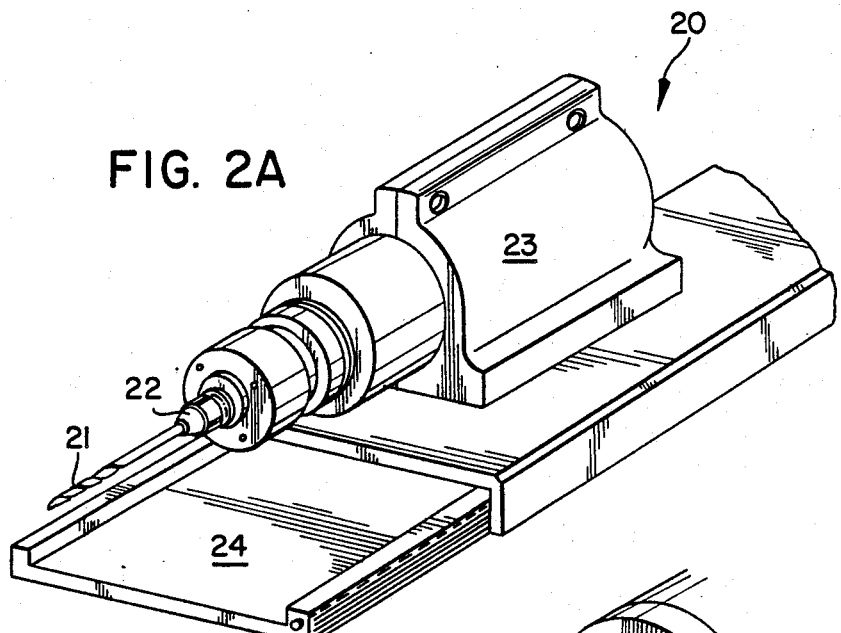
FIG. 2A
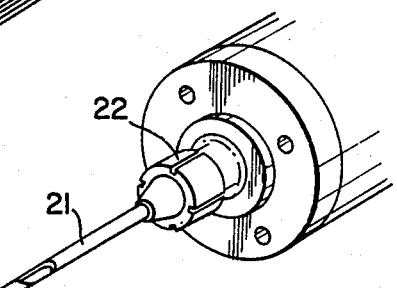
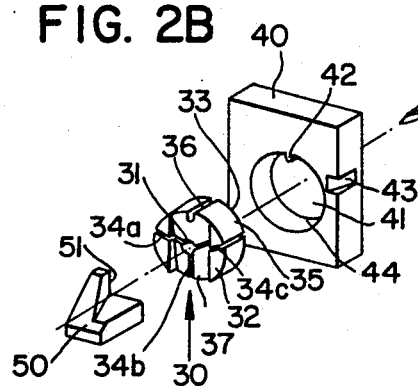
FIG. 2B
FIG. 2B'
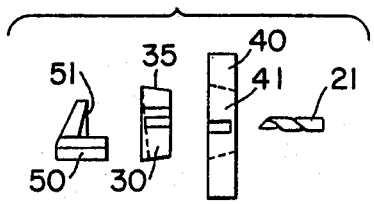
FIG. 2C

APPARATUS FOR FORMING A SUTURE CUT-OFF FEATURE IN A SURGICAL NEEDLE POSSESSING A SUTURE-RECEIVING SOCKET

CROSS REFERENCE TO RELATED APPLICATION

This application relates by subject matter to commonly assigned, concurrently filed U.S. patent application Ser. No. 317,948, filed Mar. 2, 1989, the contents of which are incorporated by reference herein.

BACKGROUND OF THE INVENTION

This invention relates to apparatus for forming a suture cut-off feature as an integral part of a suture-receiving socket previously or concurrently formed within the blunt end of the surgical needle component of a combined surgical needle-suture device The prior art describes a variety of arrangements for securing a suture within an axial socket, or recess, drilled into the blunt end of a surgical needle and for providing release, or separation, of the needle from the suture upon completion of suturing. Illustrative of such suture-surgical needle combinations are those described in U.S. Pat. Nos. 1,757,129; 3,799,169; 3,910,282; 3,926,194; 3,943,933; 3,949,756; 4,054,144; and, 4,072,041. Specific techniques provided in these prior disclosures for achieving separation of the needle from the suture include peeling the suture out of a channel formed in the rear of the needle as shown in U.S. Pat. No. 3,799,169 and tugging sharply at the needle within some predetermined range of "pull-out" force to effect separation of the needle and suture at the site of a weakened suture segment as shown in U.S. Pat. Nos. 3,926,194; 3,943,933; 3,949,756; 4,054,144; and, 4,072,041.

U.S. Pat. No. 2,910,983 describes a suture surgical needle combination in which the suture is held securely within a crimped socket possessing an outer sharp circumferential edge. The sole disclosed function of the sharp edge is to provide a flared entrance to the socket thus preventing damage to the suture. There is no suggestion in U.S. Pat. No. 2,910,983 of providing a sharp edge for the purpose of achieving suture cut-off.

SUMMARY OF THE INVENTION

It is an object of the invention to provide an apparatus for forming a suture cut-off feature integrally associated with a suture-receiving socket formed in the blunt end of a surgical needle intended to receive, and retain, the tip of a suture therein.

It is a particular object of the invention to provide an apparatus for forming a circumferential cutting edge at the entrance to the suture-receiving socket which is capable of severing the suture retained within the socket when separation of the needle from the suture is desired.

It is another particular object of the invention to provide a collect for receiving and firmly gripping the socketed end of a surgical needle and accurately maintaining the position of the socketed end of the needle relative to a tool during suture cutting edge forming operation.

In keeping with these and other objects of the invention, there is provided an apparatus for forming a suture cutting edge at the entrance of a suture-receiving socket of a surgical needle which comprises:

(a) tool means for forming the suture cutting edge;
(b) surgical needle receiving and holding means which, in a locked position, accurately maintains the position of the socketed end of the needle relative to the tool means during the suture cutting edge forming operation;
(c) means for locking the socketed end of the needle within the surgical needle receiving and holding means; and,
(d) means for advancing the tool means relative to the socketed end of the needle by a predetermined distance.

In operation, a surgical needle is inserted socketed end-forward into the needle receiving holding means of the foregoing apparatus. Activation of the needle locking means provides precise alignment of the socketed end of the needle with the cutting edge forming tool so that with axial movement of the latter relative to the former through a predetermined distance, a circumferential cutting edge is formed which is integral with the entrance to the suture-receiving socket.

The demands of precision, accuracy and dependability which are imposed upon the apparatus herein in forming a suture cut-off feature in a surgical needle of the socketed type are fairly prodigious as can be readily appreciated from the Table, infra, setting forth typical needle dimensions. In meeting these demands with a high degree of reliability, the apparatus of the present invention represents a significant development in the art of surgical needle manufacture.

DESCRIPTION OF THE PREFERRED EMBODIMENTS

The apparatus of the present invention and its operation will be specifically described in connection with the manufacture of a preferred type of surgical needle, i.e., the socketed needle possessing a suture cut-off feature which is described in aforementioned commonly assigned, concurrently filed U.S. patent application Ser. No. 317,948, filed Mar. 2, 1989 and in FIGS. 1A and 1B herein.

Figure 1A:
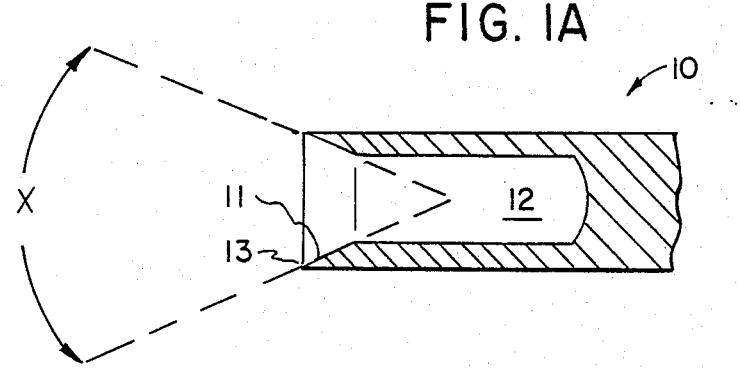
FIGS. 1A and 1B are enlarged cross sectional views of the axial suture-receiving socket end of a preferred type of surgical needle component of a surgical needle-suture combination manufactured by the apparatus of this invention showing the side profile of the socketed end of the needle before (FIG. 1A) and after (FIG. 1B) attachment of the tip of the suture to the needle.
Figure 1B:
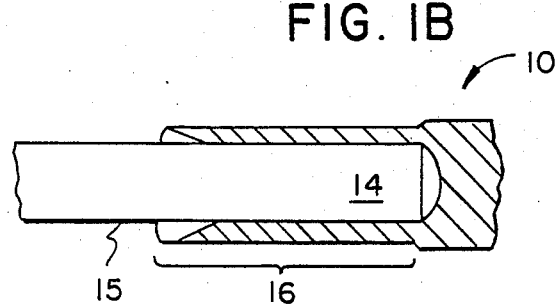

As shown in FIG. 1A, the rear portion of surgical needle 10 possesses a sloping surface 11 defining the entrance to a concentrically positioned socket 12. Sloping surface 11 terminates in a circumferential cutting edge 13 which possesses an inclusive angle x formed at the junction of opposed sloped surfaces. The cutting edge can be smooth as shown or it can be notched or serrated to enhance its cutting action. In FIG. 1B, tip 14 of suture 15 is shown occupying socket 12 of needle 10 and is held tightly within the socket by a crimping of needle section 16 about the tip of the suture, e.g., as described in U.S. Pat. No. 3,736,646. Crimping has no appreciable affect upon the value of inclusive angle X. To effect separation of the needle from the suture, the suture is oriented relative to the needle such that the suture is made to bear against any location along the circumferential cutting edge of the needle socket entrance and, while the suture is held in tension against the cutting edge, an arc-like, or sweeping, movement of the suture against the cutting edge is employed to effect separation of the needle from the suture at their junction.

Aforesaid angle x which defines the slope of the socket entrance is critical to achieving effective suture cut-off. If, on the one hand, the value for inclusive angle X is below a certain minimum (which depends upon the structural/mechanical properties of the material from which the needle is fabricated and can be readily determined in a given case by simple and routine testing), the slope of the socket entrance will be too steep for the needle material in the vicinity of the socket entrance to withstand the force of the tensioned cutting movement which is employed to sever the suture upon the circumferential cutting edge. If, on the other hand, the value for inclusive angle X exceeds a certain maximum (again, as in the case of the minimum value of X, a variable which depends to some extent upon the nature of the material from which the needle is fabricated and is readily determined for a specific needle construction by simple, routine testing), the slope of the socket entrance will be too shallow to provide an effective cutting edge. For surgical needles manufactured from any of the stainless steels which are commonly used for the construction of such needles, the value of inclusive angle X is advantageously on the order of from about 90° to about 120° and preferably is from about 95° to about 105°. The needle can possess any appropriate shape, e.g., it can be straight or it can possess a largely curved configuration.

Typical needle dimensions for a variety of suture sizes are set forth in the following table.

about 0.00015 inches. The drill together with its motor is supported upon a linear bearing member 24 which permits movement of drill 21 toward and away from the rear face of a socketed needle, e.g., with a straight line accuracy of at least 0.0005 in./in. of travel, as shown in FIG. 2D.

Figure 2D:
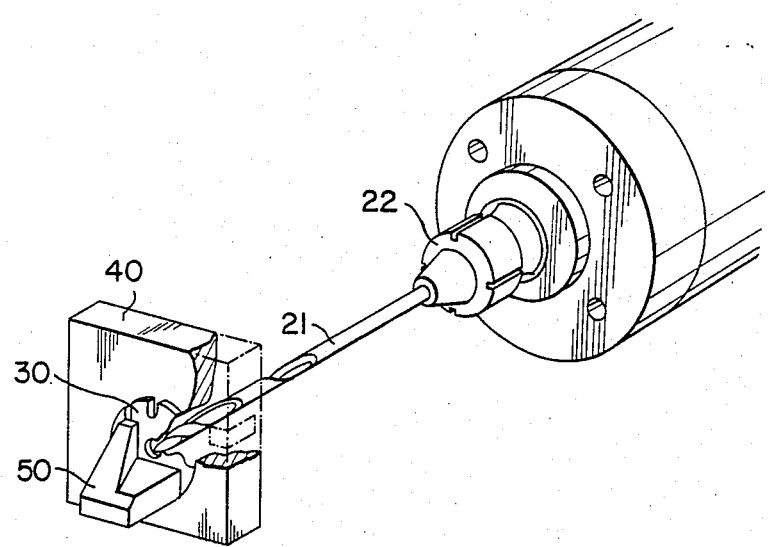
FIG. 2A is a perspective view of an axially movable cutting edge forming tool for use in the apparatus of this invention.
FIG. 2B is an exploded perspective view of the principal elements of the cutting edge forming apparatus of the invention.
FIG. 2C is an exploded side elevational view of the locking ram, collet and collet holder elements of the apparatus of FIG. 2B; and, FIG. 2D is a perspective view of the assembled apparatus of FIG. 2B.

As shown in FIGS. 2B–D, needle receiving and holding collet 30 possesses a central bore 31 extending its full length for receiving the socketed end of a surgical needle. The collet possesses three slots 34a, 34b and 34c extending from its front face 33 to rear face 32 along conical shaped wall 35. These slots enable the collet to convert an axially directed force exerted against its rear face 32 to a circumferentially compressive force exerted against the blunt end of a needle present within bore 31 whereby the needle is held firmly and accurately in place within the collet for the subsequent circumferential suture-cutting edge-forming operation (as well as any optional socket forming operation). Collet holder 40 functions as a support frame for collet 30 and orients and guides the axial movement of the collet upon activation of locking ram 50. Opening 41 in collet holder 40 possesses a conical configuration providing an accurate mating support surface for collet 30 and permitting a limited degree of forward, axial movement of the collet therein when locking ram 50 is set in motion. Key 42 along the periphery of opening 41 of collet holder 40 cooperates with slot 36 in the collet to precisely orient the collet and make certain that the socketed end of the needle held within the collet is accurately positioned relative to drilling tool 21. Clearance slot 43 is provided on the collet holder in order to fully accommodate a curved needle during the machining thereof.

To accomplish locking of the needle within the collet and locking of the collet within its holder, a vertical movement of locking ram 50 against the upwardly sloping surface 37 of rear face 32 of collet 30 causes an axial forward movement of the collet within opening 41 of collet holder 40. Activation of locking ram 50 results in the application of an amount of force against collet 30 which is sufficient to slightly compress the sections of the collet as defined by slots 34a, 34b and 34c thereby securely locking the needle in place for drilling.

TABLE

Needle Dimensions

| Suture Size Designation | Suture Diameter | | Needle Diameter, inches | Socket Diameter, thousands of an inch (mils) | Socket Depth, inches |
| --- | --- | --- | --- | --- | --- |
| | mm | inches | | | |
| 6-0 | 0.070–0.099 | 0.0026–0.0039 | 0.013 | 6.4–7.0 | 0.030 |
| 5-0 | 0.10–0.149 | 0.0039–0.0059 | 0.015 | 8.8–9.6 | 0.035 |
| 4-0 | 0.15–0.199 | 0.0059–0.0078 | 0.017 0.022 | 10.2–11.0 | 0.042 |
| 3-0 | 0.20–0.249 | 0.0079–0.0098 | 0.024 0.039 | 12.5–13.5 | 0.050 |
| 2-0 | 0.030–0.339 | 0.0118–0.0133 | 0.026 0.039 0.050 | 15.2–16.2 | 0.057 |
| 1-0 | 0.35–0.399 | 0.0138–0.0157 | 0.039 0.044 0.050 | 18.2–19.2 | 0.060 |
| 1 | 0.40–0.499 | 0.0157–0.0196 | 0.039 0.044 0.050 | 21.2–22.2 | 0.070 |

As shown in the apparatus of FIG. 2A, drilling unit 20 is provided as a fluted drill bit 21 held in spindle 22 of a high speed motor 23. Spindle 22 should be capable of holding drill 21 with considerable accuracy, e.g., with a maximum positional variation of no more than The geometries of those surfaces of collet 30, collet holder 40 and locking ram 50 which come into mutual contact during the locking step are important to achieving effective and accurate locking. Thus, the forward face 51 of locking ram 50 is so shaped as to present a downwardly sloping angle, in the embodiment shown, 5°, corresponding to the 5° angle of upwardly sloping surface 37 formed on the rear face 32 of collet 30. As the driving ram moves upwardly along a vertical axis which is perpendicular to the longitudinal axis of the collet, the resulting engagement of mating surfaces 51 and 37 forces collet 30 forward within the collet holder, the 9°30′ slope of collet wall 35 engaging the 9° wall 44 of collet holder 40. The slightly greater angle of wall 35 of collet 30 relative to that of wall 44 of collet holder opening 41 results in the application of a transversally directed spring-like compressive force against collet 30 upon activation of locking ram 50 which firmly locks the needle in place.

When locking ram 50 is lowered, i.e., returned to the unlocked position, release of the compressive force against collet 30 results in rearward movement of the collet within collet holder 40 accompanied by a rearward ejection of the needle, now possessing a circumferential suture-cutting edge, from the collet bore.

In the embodiment shown, positional needle tolerance in the locked condition of the apparatus is held to a maximum deviation from the longitudinal axis of the needle of not more than about 0.00025°. Thus, the apparatus of this invention makes it possible to obtain very accurate positioning of the blunt end of the needle relative to the drill and to maintain this position throughout the socket and circumferential suture-cutting edge-forming operations. In the enlargement of the tip of drill 21 shown in FIG. 2B, the included angle formed by the sloping surfaces of the drill is established so as to define the value of inclusive angle x of the slope of the socket edge. In the embodiment shown, this angle is set at 100°.

During the cutting edge forming operation minute metal shavings or particles may tend to lodge within the socket. Prior to inserting the suture within the socket, it is preferred to remove these shavings employing any effective technique, for example, an ultra sonic cleaning operation.

What is claimed is:

1. An apparatus for forming a suture cutting edge at the entrance of a suture-receiving socket formed in the blunt end of a surgical needle which comprises:
   (a) tool means for forming the suture cutting edge;
   (b) surgical needle receiving and holding means which, in a locked position, accurately maintains the position of the socketed end of the needle relative to the tool means during the suture cutting edge forming operation, the surgical needle receiving and holding means comprising a conical shaped collet possessing an axially extending, centrally disposed needle-receiving bore for its full length and open at each end thereof, the collet possessing a plurality of slots extending from its front to its rear face and capable of undergoing compression upon application of a compressive force to firmly lock the blunt end of the needle within the bore;
   (c) means for locking the socketed end of the needle within the surgical needle receiving and holding means; and,
   (d) means for advancing the tool means relative to the socketed end of the needle by a predetermined distance 2. The apparatus of claim 1 wherein tool means (a) includes a fluted drill bit.

3. The apparatus of claim 1 further comprising a collet holder (e) possessing a conical opening for receiving the collet in surface contacting engagement therewith, the collet holder permitting limited forward movement of the collet therein such that application of a force to the collet which drives the collet forward within the collet holder imparts a compressive force to the collet locking the needle within the bore thereof.

4. The apparatus of claim 1 wherein means (d) for advancing the drilling means relative to the blunt end of the needle includes a linear bearing supporting said drilling means.

5. An apparatus for forming a suture cutting edge at the entrance of a suture-receiving socket formed in the blunt end of a surgical needle which comprises:
   (a) tool means for forming the suture cutting edge;
   (b) surgical needle receiving and holding means which, in a locked position, accurately maintains the position of the socketed end of the needle relative to the tool means during the suture cutting edge forming operation, the surgical needle receiving and holding means comprising a conical shaped collet possessing an axially extending, centrally disposed needle-receiving bore for its full length and open at each end thereof, the collet possessing a plurality of slots extending from its front to its rear face and capable of undergoing compression upon application of a compressive force to firmly lock the blind end of the needle within the bore;
   (c) a collet holder possessing a conical opening for receiving the collet of surgical needle receiving and holding means (b) in surface contacting engagement therewith, the collet holder permitting limited forward movement of the collet therein such that application of a force to the collet which drives the collet forward within the collet holder imparts a compressive force to the collet locking the needle within the bore thereof;
   (d) means for locking the socketed end of the needle within the collet of surgical needle receiving and holding means (b), said locking means comprising a locking ram possessing a downwardly sloping front surface which, in the locking position of the ram, makes mating engagement with an upwardly sloping surface defined upon the rear face of the collet forcing the collet forward with the collet holder; and,
   (e) means for advancing tool means (a) relative to the socketed end of the needle by a predetermined distance.

6. The apparatus of claim 5 wherein tool means (a) includes a fluted drill bit.

7. An apparatus for forming a suture cutting edge at the entrance of a suture-receiving socket formed in the blunt end of a surgical needle which comprises:
   (a) drilling means for forming the suture cutting edge, the drilling means including a fluted drill bit driven by a high speed motor;
   (b) a conical shaped collet for receiving, and in its locked position, for firmly holding, the socketed end of a needle received therein, said collet possessing an axially extending, centrally disposed needle-receiving bore for its full length and open at each end thereof, the collet possessing a plurality of slots extending from its front to its rear face and capable of undergoing compression upon application of a transversally directed compressive force to firmly lock the blunt end of the needle within the bore;
   (c) a collet holder possessing a conical opening for receiving collet (b) in surface contacting engagement therewith, the collet holder permitting limited axial forward movement of the collet therein such that application of an axially directed force to the collet which drives the collet forward within the collet holder imparts a transversally directed compressive force to the collet locking the needle within the bore thereof;

(d) a locking ram possessing a downwardly sloping front surface which, in the locking position of the ram, makes mating engagement with an upwardly sloping surface defined upon the rear face of col].et (b) forcing the collet forward within collet holder (c) to thereby impart a transversally directed compressive force to the collet and firmly lock the needle present within the bore thereof into position; and, (e) a linear bearing supporting drilling means (a) and permitting the advance of the drilling means toward the blunt end of the needle by a predetermined distance.

8. The apparatus of claim 2 wherein the sloping surfaces of the fluted drill bit define an inclusive angle x possessing a value of from about 90° to about 110°.

9. The apparatus of claim 7 wherein the sloping surfaces of the fluted drill bit define an inclusive angle x possessing a value of from about 90° to about 110°.

10. The apparatus of claim 6 wherein the sloping surfaces of the fluted drill bit define an inclusive angle x possessing a value of from about 90° to about 110°.

11. The apparatus of claim 5 wherein means (e) for advancing the drilling means relative to the blunt end of the needle includes a linear bearing supporting said drilling means.

* * * * *